(12) United States Patent
Dronzek, Jr. et al.

(10) Patent No.: US 8,496,947 B2
(45) Date of Patent: Jul. 30, 2013

(54) DENTAL WHITENING STRIPS

(75) Inventors: Peter J. Dronzek, Jr., New Milford, CT (US); Leonard B. Gross, Fort Lee, NJ (US); Leslie U. Fernandez, Putnam Valley, NY (US)

(73) Assignee: Creative Specialty Products, LLC, Lewes, DE (US)

( * ) Notice: Subject to any disclaimer, the term of this patent is extended or adjusted under 35 U.S.C. 154(b) by 175 days.

(21) Appl. No.: 11/891,730

(22) Filed: Aug. 13, 2007

(65) Prior Publication Data

US 2008/0057092 A1      Mar. 6, 2008

Related U.S. Application Data

(60) Provisional application No. 60/839,027, filed on Aug. 21, 2006.

(51) Int. Cl.
*A61K 8/22* (2006.01)
*A61K 8/02* (2006.01)
*A61Q 11/00* (2006.01)

(52) U.S. Cl.
USPC .......................................... 424/401; 424/53

(58) Field of Classification Search
USPC .......................................................... 424/40
See application file for complete search history.

(56) References Cited

U.S. PATENT DOCUMENTS

| | | | |
|---|---|---|---|
| 2001/0053375 A1* | 12/2001 | Sagel et al. | 424/401 |
| 2002/0187108 A1* | 12/2002 | Rajaiah et al. | 424/49 |
| 2003/0107149 A1* | 6/2003 | Yang et al. | 264/134 |
| 2004/0037789 A1* | 2/2004 | Moneuze et al. | 424/49 |
| 2004/0136924 A1* | 7/2004 | Boyd et al. | 424/48 |
| 2005/0208110 A1* | 9/2005 | Singh et al. | 424/443 |
| 2005/0260266 A1 | 11/2005 | Gebreselassie | |
| 2005/0281757 A1 | 12/2005 | Ibrahim | |
| 2006/0099154 A1 | 5/2006 | Kahwaty | |

OTHER PUBLICATIONS

PCT Search Report dated Mar. 3, 2008.
PCT International Preliminary Examination Report Mar. 5, 2009.

* cited by examiner

*Primary Examiner* — Walter Webb
(74) *Attorney, Agent, or Firm* — Hedman & Costigan, P.C.

(57) ABSTRACT

A dental whitening strip which includes a carrier support having a whitening composition adhered to said carrier where the whitening composition comprises
 (a) dextrin;
 (b) a peroxide;
 (c) a non-toxic water soluble inorganic salt;
 (d) a acceptable hydroxy compound which is a plasticizer.

17 Claims, 1 Drawing Sheet

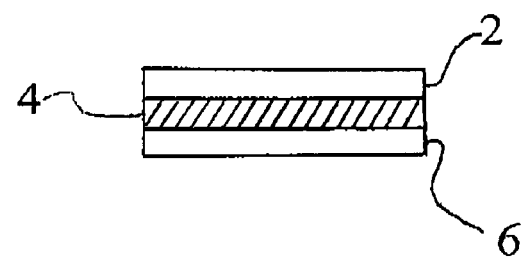

DENTAL WHITENING STRIPS

FIELD OF THE INVENTION

The present invention relates to a consumer friendly disposable dental whitening strip with an active stain removing coated matrix layer formulated from a natural polymer that removes stains when the strip is affixed to the teeth. More particularly, the invention relates to a semi-dry controlled volatile content hybrid strip that is not of the dry type or gel type currently on the market which provides for exceptional quick stick adhesion over the dry type without the messy handling characteristics of the gel type. The strip comprises a volatile (peroxide, water and propylene glycol) controlled multi-layer structure with an active side and a support side. The support side consists of a thin flexible low density extruded film. The film in addition to providing support for the active layer, also provides barrier to maintain the active layer against the teeth while not contacting other areas of the oral cavity.

The active layer is a formulated coating matrix containing peroxide for whitening action based on bleaching that is achieved with repetitive applications of the strip on a daily basis from 7-42, preferably from 7-21 days based on the peroxide concentration. It surprisingly has been found that a coating matrix comprising a natural polymer of USP and food grade approved modified starch functions as a superior adhesive to affix the strip to the teeth while providing a stable binder to contain the peroxide which at a 6-10% active level is not a strong oxidizer in the coating matrix. While the modified starch polymer provides strong adhesive attachment to teeth, it releases the tooth whitening agent when the active layer is hydrated by the saliva on the teeth.

The barrier support layer of the strip consists of a thin flexible low density extruded film that conforms to and maintains the active layer against the teeth in intimate contact with the surface to be whitened while not contacting other areas of the oral cavity. The controlled volatile content strip of the present invention can be constructed with white, transparent or colored flexible support barrier film. Transparent contact clear is preferred so the strip can be worn in public areas without easy detection so the whitening system can be used while people are at work, on a bus, etc.

BACKGROUND OF THE INVENTION

The most common tool for dental hygiene is the toothbrush where mechanical action of the toothbrush bristles aids in the removal of food particles, plaque and stains. The toothbrush is normally used with a toothpaste which in early years consisted of a surfactant and an abrasive material intended to augment the mechanical action of the brushing.

Various active ingredients have been incorporated into toothpaste such as fluoride, tartar control agents and peroxide to provide further dental hygiene and oral care benefits. As people's interest in whitening teeth has increased, various versions of toothpaste having tooth whitening properties have become commercially available. Even though the toothpaste contains a tooth whitening agent, it is hard to achieve a significant whitening effect in a short period of time by brushing teeth for 1 to, 3 minutes of contact time between teeth and toothpaste.

Consumers have turned their attention to the cosmetic aspects of dental care, such as tooth whitening. One expensive consumer option is professional tooth whitening programs provided by dentists. They generally consist of an in-office bleaching procedure or an outside-the-office bleaching procedure. The in-office procedure involves several visits, each of which begins with the fabrication of a specially fitted rubber dam within the mouth to prevent the whitening chemicals that have bleaching action, typically hydrogen peroxide, from contacting the soft oral tissue. The production of the rubber dam within the patient's mouth may be both uncomfortable and time consuming. The strength of the peroxide bleach mandates the use of the dam. The in-office procedure may also leave the teeth sensitive to heat and cold and is very expensive.

The outside-the-office whitening program differs in that the patient applies the bleaching agent to his or her own teeth using a lower strength chemical bleaching agent over an extended period of time, typically several hours a day for several weeks. The outside-the-office program typically requires an initial fitting in the dentist's office for a device which is specific to the particular patient. The device is fabricated to fit precisely onto the patient's teeth and is used to deliver a bleaching product to the patient's teeth such as a gel containing a hydrogen peroxide complex. The patient is responsible for measuring and applying the bleaching agent to the surfaces of the teeth using the device as the means for delivery and containment. The reusable device must be durable to endure repeated handling, cleaning, filling, installation, and wearing. The device is typically rigid in order to maintain fit during repeat use and in many cases can cause discomfort and gum irritation.

There are now non-professional programs available to persons interested in whitening their teeth using commercial products available at drug stores. The commercial products provide a kit which includes a generic appliance and a container of bleaching gel. The obvious appeal is the lower cost of the program. A major disadvantage of this "one size fits all" appliance is the greater void between the interior walls of the appliance and the teeth versus the professionally fitted appliance. In order to insure intimate contact of the bleaching gel and the teeth surfaces, more bleaching gel is required. Furthermore, the poor fit means a greater loss of bleaching gel onto the gums, into the oral cavity, and eventual ingestion. The commercial kits, like the outside-the-office professionally administered program, require the user to clean and to reuse the appliance. Since generic appliances are not fitted to the individual user, they are even more bulky in the mouth than the fitted appliances and thus they restrict social discourse to a greater degree.

One attempt to remedy some of the problems of the commercial kits is disclosed in U.S. Pat. No. 5,575,654, issued to Fontenot on Nov. 19, 1996. Fontenot discloses a prepackaged moldable dental appliance, adapted to fit a wide range of variously sized dental arches, which contains a premeasured amount of medicinal or bleaching agent. In use, the dental appliance is removed from the packaging, aligned in a parallel fashion to the edges of the teeth and pushed over the teeth in the direction of the periodontal tissue until it covers the teeth surfaces. The primary benefit of the device disclosed by Fontenot is elimination of the measuring and filling of the appliance and the disposability after each use.

Japanese Patent No. 12-281,548, filed on Mar. 16, 1999 and published on May 30, 2000, discloses a tooth whitening kit set utilizing devices such as water-insoluble tape, sheet, film, dental tray, mouth tray, mouthpiece, impression pack, pack material, and chewing brushing having a plurality of protrusions on a surface contacting with the teeth. The invention requires thinly applying a whitening component in a wet gel phase to a supporting layer of the above devices or by immersing the adhesion portion of the above devices in a solution containing a whitening agent which means the devices claimed in this patent are wet type. When using devices like this, it is unduly cumbersome and the whitening agent can contact the hands or other body parts causing irritation.

U.S. Pat. Nos. 5,310,563 and 5,639,445, assigned to Colgate-Palmolive company, disclose a dental material comprising an active component dispersed in a polysiloxane polymer composition sold by Dow Corning Corporation under the trade name Dow Corning 3179 Dilatant Compound which is attached to the teeth by pressing it against the teeth and the gum. It is easily removed from the teeth without breaking into pieces and adhering to tooth surfaces. The material has the active component encapsulated in the polymer whereby the active component cannot be easily released necessitating extended contact time in order to obtain a tooth whitening effect.

U.S. Pat. Nos. 5,879,691, 5,891,453 and 5,989,569 assigned to Procter & Gamble disclose a delivery system for a tooth whitener, comprising a transparent, thin and flexible polyethylene strip having a professional whitening gel and the like thereon, wherein the professional whitening gel is pre-coated in a manufacturing process or applied directly by the wearer before attaching the strip to teeth. Since it does not use a mouth tray, user friendliness is improved but it is still a wet gel system that requires special handling and precaution. The strip is thin and transparent so daily life is not interrupted when wearing the strip. Reviewing the examples, the invention of these patents is considered a wet type liquid tooth-whitening system constructed by using a tooth whitening substance along with a synthetic gelling agent, preferably carboxypolymethylene, obtained from B.F. Goodrich Company under trade name of Carbopol to form a liquid gel along with water, pH adjusting agent and carrier materials which is then applied wet onto a strip of flexible material. When handling this type of system or attaching and wearing the system on the teeth, the gel containing peroxide at a high concentration as a tooth whitener may transfer and adhere to the hands, tongue, gum and the like. Therefore, there is room for improvement in handling and application.

U.S. Pat. Nos. 6,682,721 and 6,780,401 assigned to LG Household And Healthcare Ltd. disclose a dry type patch for tooth whitening that overcomes the limitations and undesirable handling and safety characteristics of the wet gel methods noted above. Unfortunately, while the dry type strip is consumer friendly in terms of safety, application and use, the product uses costly ingredients applied at low solids that raise the cost of manufacturing. The dry LG product has less of a market share than the wet gel systems because of the cost of manufacturing. This is because the patented formulation comprises expensive raw material synthetic-polymers and a multi-step coating process for the active layer and the backing layer that is very costly. While this dry strip is a better product design than the wet system of Proctor & Gamble because it is easier to use and will be preferred by the consumer, manufacturing cost and market economics appear to have kept LG, a worldwide consumer products giant from penetrating the U.S. and European markets and have limited the success of the dry strip technology to a minor almost negligible share in Asia.

The whitening strips used in the market today are divided into two categories: a wet gel type like the Proctor & Gamble product and a dry type like the LG product described above. The wet type strip is for example, a hydrogel formulation such as a high viscosity gel applied to a film backing, or a formulation formed by applying a gel to an adhesive layer or immersing an adhesive layer in a solution. This type of strip is considered wet since the content of water or ingredients in the formulation such as glycerin is high and the fluid gel will flow and transfer. This type of strip is messy because of free gel or fluid and is not preferred by the consumer. The wet formulation generally lacks strong adhesion strength and relies on high viscosity for adhesion. Since it is sticky in its initial state, when a user handles it, gel may adhere to hands when attaching the strip to the teeth. When a user fumbles about to try to attach the strip to the contours of the teeth, a gel formulation including peroxide at a high concentration may adhere to undesired areas such as hands, mucus membranes, lips, tongue, etc, causing irritation.

The dry type strip such as the LG product defined above is characterized in final form by the fact that it solid and not liquid and has low levels of retained volatiles versus the wet gel system. The dry strip is defined by not being liquid and containing less than 6% retained volatiles as packaged not including peroxide based on studies of dry strips commercially available from Asia.

SUMMARY OF THE INVENTION

According to the present invention, there is provided a novel hybrid strip for tooth whitening, comprising dextrin (a natural converted starch based polymer) as the binder for the whitening strip. A low density conformable extruded packaging film used as the barrier support for the coated dextrin based active coating matrix containing the peroxide whitening agent attains stable peroxide levels either by using a stabilizer for peroxide or by selecting a dextrin that has good compatibility with peroxide. The whitening strip comprising the coated active layer adhered to the barrier support is laminated to a carrier layer sandwiching the active layer between the two films.

According to the present invention, as a barrier and support layer, a film formed by extrusion of low density flexible resins into a film is used. The barrier and support layer helps prevent the active layer, that also functions as the adhesive layer, from adhering to the gum, tongue, inner lip and mucus membranes and further prevents the strip from deforming, prematurely becoming soluble in the mouth during the recommended use time or from being detached from teeth by excess saliva. The invention provides a dental whitening strip which comprises a barrier support having a whitening composition which adheres to said barrier, said composition comprising:
(a) dextrin;
(b) a peroxide;
(c) a non-toxic water soluble inorganic salt; and
(d) a hydroxy compound which is a humecant The invention also provides a novel composition for making a tooth whitening strip which comprises:
(a) dextrin;
(b) a peroxide;
(c) a non-toxic water soluble inorganic salt;
(d) a hydroxy compound which is a humecant; and
(e) an amount of water to enable the active layer to be adhered to a carrier layer.

It is an object of the present invention to provide a hybrid strip for tooth whitening which is safe after the active layer becomes wet and partially soluble where residual amounts of the active layer can be ingested.

It is also an object of the invention to provide a novel composition for making a tooth whitening composition.

These and other objects of the invention will become apparent for the appended specification.

BRIEF DESCRIPTION OF THE DRAWINGS

FIG. 1 is a cross-sectional schematic of a hybrid tooth whitening strip according to the invention.

DETAILED DESCRIPTION OF THE INVENTION

For purposes of this invention, a semi-dry controlled volatile content hybrid strip hereafter denoted the "hybrid strip" is defined as having greater than 7% and less than 17% retained volatiles excluding the amount of peroxide in the semi-dry active layer coating matrix as packaged, when the volatiles are measured according to the method described herein. The present invention has advantages such as superior adhesion strength to the teeth in the moist oral cavity while simplifying handling to avoid whitening agents adhering to hands or other places such as gums, mucus membranes and tongue in the oral cavity as compared to the gel whitening strips of the prior art.

In order to produce the hybrid type strip of the current invention economically for commercial success, it is necessary to select a polymer as binder for the coating matrix containing the active whitening ingredient that provides a high solids composition for ease of processing and is able to rapidly bond to the tooth surface with strong adhesion when hydrated by a small quantity of saliva while having little or no adhesive strength in the semi-dry state. The polymer should begin to release the tooth whitening agent when hydrated. Starch polymer derived from plants converted into dextrin through acid or enzyme treatment, roasting and or other means is an excellent choice of polymer for this purpose.

The current invention allows for the efficient manufacturing and marketing of the hybrid tooth whitening strip of the present invention. It utilizes readily available foodstuff ingredients combined with peroxide for the active layer in a simple one step coating and laminating process using dextrin starch natural binder for a high solids active layer. The active layer is coated onto a low density polyethylene packaging film as a barrier support that is then laminated to a carrier film. The active layer of the strip material is coated directly onto the barrier support low density polyethylene film, dried to drive off carrier moisture to the desired retained volatile level and is then laminated to the carrier. Alternatively, the active layer can be coated onto the carrier layer, dried to the desired retain volatile level and laminated to the barrier support layer. Adhesion of the active layer develops to the barrier support greater than the adhesion to the carrier so the strip can be removed from the carrier at the point of end use. Depending on the choice of the carrier, it may or may not have a release coating to facilitate easy removability of the strip. The carrier typically will be a film substrate such as a polyolefin (polypropylene or high density polyethylene or a blend) or polyester which are firm films that are readily used in die cutting. The strip is cut to shape smaller than the size of the carrier film to provide a means for easy detachment. Critical to the efficient manufacturing process of the invention is the lamination step that requires the active layer of the hybrid strip to have greater than 7% retained volatiles less peroxide which will predominantly be moisture to partially activate the coating matrix into an adhesive so it has sufficient tack to bond the barrier support layer to the carrier layer with the active layer in-between. The range of 7-17% volatiles less peroxide is the working range for the active layer of the hybrid strip. It has been determined that 7% is the minimum amount of retained volatile (predominantly moisture) needed for the active layer to firmly adhere the barrier and carrier film layers together. Greater than 17% retained volatiles causes the active layer to be over hydrated causing it to become gel like and soft with loss of cohesive strength possibly leading to transfer to the carrier. In this state, the active layer becomes aggressive and sticky to the touch and is difficult to remove from the carrier.

The high solids dextrin based coating matrix forms a layer that does not flow and does wet objects when touched. When the retained volatiles are between 7-17% not including the peroxide content. This allows for efficient manufacturing in coating and drying through lamination in contrast to the preferred dry strips of the current art that require multiple coating steps because the support layer is also coated instead of a preformed film of the current invention.

In a later step, the laminated structure with the active dextrin based layer between the carrier and barrier support films is subsequently die cut into the desired shape of the strip. The excess matrix material around the die cut shape of the strip is removed. After die cutting, the strip is packaged in a sealed barrier package to prevent the active ingredients and retained volatiles from dissipating over time, especially in changing environmental conditions.

In end use, the die cut strip of whitening material is removed from the barrier package, peeled off the oversized carrier and applied by the end user to an entire tooth, or to a row of adjacent teeth. The side of the hybrid strip facing the tooth is coated with the active dextrin starch based tooth whitening layer. The dextrin starch not only is the binder layer for the active whitening ingredient or ingredients but it also functions as the adhesive to adhere the strip to the teeth which is activated when the hybrid strip coated layer comes into contact with the saliva on the tooth surface. The saliva on the surface of the teeth wets the dextrin binder creating the adhesive properties. In summary, the dextrin performs multiple functions. It binds and contains the active ingredient(s) of the coating matrix. It also provides the adhesive properties first before use between the barrier support and carrier films and finally between the tooth surfaces and the hybrid strip during use in order to hold the strip of material in place firmly.

Using a low density polyethylene film coated with the active layer which adds considerable thickness and stiffness that has a flexural stiffness (Gurley stiffness) less than about 20 grams/centimeter and preferably in the range of 3-10 grams/centimeter as measured on a Handle-O-Meter, available from Thwing-Albert Instrument Co. of Philadelphia, Pa. provides for exceptional conformability of the strip to the teeth and intimate contact of the active layer to the tooth surface. The low density polyethylene flexible strip of material of the present invention that delivers the active ingredient is readily conformable without permanent deformation to conform to the shape of a tooth when the dextrin layer containing the active whitening ingredients is placed against the saliva wetted teeth providing intimate contact between the active layer and surface to be bleached on the surface of the teeth. The dextrin binder of the coating matrix of the hybrid strip provides adhesive attachment between the whitening strip and the tooth surface when activated with saliva. The dextrin binder provides excellent wet adhesion and cohesiveness to hold the active layer in place for a sufficient time to allow the whitening ingredient to act upon the tooth surface. This time period is adjustable based on peroxide concentration and active total coat weight but the dextrin adhesive holds up when hydrated because it forms a gel in place after application without adhesive or cohesive failure for over an hour.

Dextrin is a natural vegetable based product formed from a converted starch that has unusual tackiness and fast setting and adhesive characteristics due to the small compact molecular size of the starch molecules A starch based carrier is an excellent choice as the active layer binder because of its film forming capability and integrity, excellent gel strength when activated, adhesive properties, ability to be ingested, and ease of commercial processing as well as a competitive cost of manufacture. Starch is a natural substance of definite chemical composition that occurs as the reserve food in most land plants. The starch is stored in plants in a number of different forms depending on the source and will vary in physical properties. Most variations are derived from corn starch, rice starch, potato starch and tapioca starch which are most commonly available.

When dry starch polymer is roasted either alone or in the presence of acid or enzymes, in a process which is known as Dextrination, the product is known as a dextrin starch which forms through a number of degradation-recombination reactions. Preferred for this invention are what are commonly known as yellow dextrins that are cold water soluble which are manufactured by heating the starch above 300° F. instead of white dextrins that are not cold water soluble and are typically heated below 300° F. during the dextrinization process. The yellow dextrin forms a higher solids, lower viscosity more stable dispersion, has superior dry film forming characteristics, stronger adhesive characteristics, good gel strength when hydrated and only moderate acidity when compared to white dextrins. The high solids nature of the dextrin based coating matrix provides for efficient manufacturing due to the rapid and more economical drying time versus the low solids active layer in the prior art employing—polymers at lower solids that want to retain moisture and are difficult to dry in the heavy coat weights used in the strip manufacturing process.

In preferred embodiments, the conformable strip of material is preferably of a size that individually fits the entire upper or lower rows of teeth when positioned against the teeth. As a soft, conformable material, the non-active strip may come into contact with the wearer's gums without causing irritation because of the barrier support layer shielding the active layer. The barrier support layer is manufactured from an extruded polymer film commercially available in high volume that is typically used for packaging. Versus the coated backing layer of the LG dry strip formed from a liquid coating, the extruded film component of the present invention provides improved barrier properties to keep the active layer in place and is much more economical to manufacture. The strip of material readily conforms to the teeth by lightly pressing it against the teeth and/or by the wearer gently sucking through the gaps between teeth to ensure intimate contact. The strip of material is easily removed by the wearer after use by peeling it off. Each successive treatment uses a fresh strip of material.

By being a relatively thin coating, the tooth whitening substance is low in volume compared to the substance contained by rigid trays fitted or unfitted. Therefore, substance is not wasted, and little of it is accidentally ingested or otherwise available for irritation of oral cavity surfaces for which it is not intended. Preferably, the strip of material and substance are substantially transparent so as to be almost unnoticeable when worn but any colored or opaque film can be used as the barrier support of the active layer. The conformability of the strip for intimate contact and the thinness of the strip enables the higher temperature of the inside of the wearers mouth to conduct heat through the strip of material to the normally cooler teeth in order to accelerate the rate of diffusion of the active whitening ingredient onto the surface of the teeth.

DESCRIPTION OF THE PREFERRED EMBODIMENTS

As shown in FIG. 1, the tooth whitening strip preferably has three layers. Layer 2 is a barrier support layer; layer 4 is a active layer of tooth whitening composition which is permanently adhered to the barrier support layer; and layer 6 is the carrier layer which is releasably adhered to the active layer.

The present invention provides a novel hybrid type strip based on natural polymer binder for tooth whitening comprising peroxide as a tooth whitening agent. In a preferred embodiment, the present invention provides a hybrid strip for tooth whitening in which hydrogen peroxide is contained as a tooth whitening agent in a natural binder coated matrix based on converted dextrin starch. The active layer is coated and supported by a flexible and conformable extruded barrier support layer which is laminated to a protective carrier film capturing the active layer between the two film layers. The dextrin polymer based active coating matrix containing the peroxide whitening agent provides strong adhesion to teeth while releasing the tooth whitening agent when hydrated on the enamel layer of teeth in the moist oral cavity.

The hybrid strip according to the present invention is convenient to use, as compared to conventional wet type strips based on gel technology. The present invention exhibits a superior adhesion to natural teeth and false teeth as compared to the gels and the dry strip of the prior while being maintained in a state attached to the teeth for an extended period of time. This assures enough contact time between the tooth whitening agent in the dextrin coating matrix that functions as an adhesive when activated and the stains on the teeth, thereby giving sufficient tooth whitening action.

All ingredients are at least food grade ingestible materials or ISP grade pharmaceutical grade fit for human use. Additionally, the hybrid strip is consumer friendly when handled by hands and fingers or while a user wears it on the teeth since the hybrid strip does not adhere to and leave residue on user's hands under normal use. The barrier film helps prevent irritation of sensitive skin in the moist oral cavity. It is a further object of the present invention to provide a hybrid strip for tooth whitening, which can be used easily and conveniently and is comfortable to the user while wearing the strip. Most importantly, the abundant supply of natural starch converted into dextrin can be formulated into a high solids active layer combined with a preformed barrier support packaging film into a hybrid strip in an efficient one step manufacturing process to form the laminate with the active layer bound between the barrier support and carrier films. This allows for commercialization of a consumer friendly hybrid strip to fill a market need so consumers do not have to work with expensive fixed tray systems or sloppy gel based strip systems.

Dextrin is a polymer derived from starch by the use of heat in the dry state and/or acids or buffers. The repeating unit of the polymer is dextrose and the weight average molecular weight is typically 4,500-85,000. Dextrin at a level of 10-75wt %, preferably 20-65wt % or more preferably 40-60wt % is employed in the whitening composition. The preferred dextrin is made from tapioca starch such as TISTAR Dextrin D-400 from TISTAR America Inc., Ridgefield, N.J. D-400 is a highly cold water soluble low viscosity dextrin used in various food and confectionary formulations. Other sources include corn starch or potato starch.

The barrier support layer is extrusion blown low density polyethylene film in the range of 0.5-5 mils thickness, preferably 1-3 mils and most preferred 2 mils. The barrier support low density polyethylene film is surface treated (corona, plasma or flame) on at least the active layer side to enhance bonding of the active layer coating matrix. It is available in food contact approved and human use approved grades from Performance Packaging, Inc., Winston Salem N.C. or Dana- Films, Westborough, Mass. Other polyolefins may also be used such as polypropylene and higher density polyethylene.

The carrier layer can be a polyolefin film in the range of 1-5 mils, preferably 2 to 4 mils such as cast, mono-axially oriented or bi-axially oriented polypropylene available from Toray Plastics America, North Kingston, R.I., High Density Polyethylene film available from KCS Industries, Langley B.C. Canada or oriented polyester film i.e. polyethylene terephthalate available from Sanyo Corp. Of America, New York, N.Y. or SKC Inc., Covington Ga., polyvinyl chloride, polytetrafluorethylene and copolymers or blends of any combination thereof. Most preferred is a carrier thickness of 3 mils. Optionally, for improved release of the hybrid strip from the carrier, the carrier can be coated with a Carnauba wax based emulsion AS35-3 from ChemCor, Chester, N.Y. or a silicone release coating system from GE Silicones, Waterford, N.Y. or Dow Corning, Midland Mich. with low extractibles that is fit for human use.

The tooth whitening effect is controlled by adjusting the thickness of the active layer and the level of active tooth whitening agent or agents. The active layer of the coating matrix of the present hybrid strip invention is intended to only be attached to the enamel surface of the teeth for the prescribed period of time based on the active ingredient concentration and thickness of the active layer. It is not intended to be attached to skin or a mucous membrane. Active peroxide levels between 4-12wt % are contemplated with coat weights of 20-90 grams/1000 sq. in, preferably 6-9 wt % at a coat weight of 40-70 grams/1000 sq. in. Most preferred is an active peroxide level of 7.5 wt % at a coat weight of 55 grams/1000 sq. in. It has been found that the preferred yellow dextrin which would be visually unpleasant to the consumer is bleached by peroxide and turns white. Through experimentation it has been determined that the bleaching action consumes 1-3% active peroxide over a period of 7 days or more.

The tooth-whitening agent in the coating matrix of the present invention contained in the active layer and may be selected from a group consisting of hydrogen peroxide, carbamide peroxide, calcium peroxide, sodium percarbonate, sodium perborate and tetrasodium pyrophosphate peroxidate. Usually, tetrasodium pyrophosphate and sodium acid pyrophosphate stabilize hydrogen peroxide without changing the intrinsic properties of the hydrogen peroxide. Also, according to the present invention, polyphosphates may be added along with peroxide as a tooth-whitening agent in order to enhance the tooth whitening effect. In general, peroxide is known to be an unstable product due to its good reactivity. Further, it typically has a poor compatibility with the many synthetic polymers of the prior. At the contemplated active peroxide range of the present invention, the peroxide is not a strong oxidizer of the dextrin and surprisingly has been found to have excellent compatibility with natural converted starch such as dextrin in the coated matrix especially when stabilized with compatible sodium acid pyrophosphate or magnesium sulfate. U.S. Pat. No. 4,320,102 teaches that peroxide is characterized by being readily decomposed through catalytic reaction with a minimal amount of metal ion contained in the active layer coating matrix composition. It has been found that for a stable peroxide containing coating matrix, the level of free metal ions must not exceed 6 mg/100 grams of dextrin and is preferably metal ion free.

The hybrid whitening strip must be packaged in barrier packaging e.g. to maintain the level of peroxide and other volatiles as time passes. The present invention uses at least one stabilizer for peroxide and preferably a combination that forms a salt with the hydroxyl ion. Magnesium sulfate which is available from Univar Corp., Clifton N.J., sodium citrate or sodium acid pyrophosphate available from Chemical Connections, Houston Tex. are the preferred stabilizers at levels up to 15% total combined weight and most preferably a combined stabilizer concentration a range of 7-9 wt %

It is noted that the hydrophilic-polymers used in the manufacture of dry whitening strips of the prior art such as PVA, PVP, HPMC. HEC, HPC. gelatin, sodium alginate, polyacrylic acid and the like can use a mixture of water and ethanol as a coating matrix carrier solvent because—the polymers, which are compatible with peroxides typically have such a great hydrophilic property that they do not coat uniformly on a surface of a release liner or other sheet so a solvent mixture of water and ethanol can solve the wetting problem to obtain a uniform coating. This is not the case for the alcohol free high solids and high viscosity solvent free dextrin based active layer of the present invention especially when a food grade wetting agent or non-ionic pharmaceutical or food grade surfactant such as Glycosperse O-20 a sorbitan mono-oleate available from Lonza Incorporated, Allendale N.J. is added to wet out low energy surfaces to which the coating matrix is applied. Preferred addition levels are 0.25-1.75% based on the total weight.

The active layer of the present invention also comprises a plasticizer to provide flexibility and crack resistance and acts as a humectant to control moisture content to prevent cracking of the coated matrix and to help maintain the volatile levels between 7-17 wt % less peroxide using a humectant addition level between 2-15% Suitable plasticizers used alone or in combination can include propylene glycol available from Stockton Sales, Monroe Township, N.J., polyethylene glycol available from Dow Chemical, Midland Mich. and glycerin available from Stockton Sales, Monroe Township N.J. propylene glycol, polyethylene glycol having a weight average molecular weight of 200-6000, preferably 200-600; polyethylene oxide having a weight average molecular weight of 100,000-200,000; sorbitol; carbopol; polaxamer; povidone, polyvinyl alcohol and mixtures of any combination thereof.

Glycerin is the preferred plasticizer alone or in combination at levels up to 15% but preferably 6-9% by weight.

Flavor additives such as Optamint-N/A, a mint flavor concentrate that is stable in the presence of peroxide is available from Symrise, Teterboro N.J. can be added at levels of 0.1-0.5%, most preferably 0.3%. The dental whitening strip composition may include a non-toxic amount of a fluoride which will reduce the incidence of dental decay when applied to the teeth. Generally from 0.05-1 wt % of a fluoride such as sodium fluoride or stannous fluoride may be used.

The preferred addition level of active peroxide is 2-20%, and preferably 6-10% by weight in the coating matrix and more preferably 8%. It has been found that 1-3% of peroxide is consumed in the bleaching action of the dextrin producing water and oxygen reducing the active peroxide level so the coating matrix formulation must take this into account.

The dental whitening strips of the invention may comprise active dental whitening agents as described herein at a levels from 1 to 20 wt % of the total weight of the whitening composition plus the weight of the barrier support layer. This range is variable depending on the active whitening agent concentration, active layer coat weight and the thickness of the barrier support layer.

For purposes of this invention, the hybrid strip is defined as having 7-17% by weight of retained volatiles in the coating matrix less peroxide which provides for a dry active layer that does not flow at room temperature and is not a liquid gel that is like the gels of the prior art and most preferably have non-peroxide containing volatiles is in the range of 7-9%.

It is contemplated that the incorporation of fine abrasive pigment particles in the active layer that can adhere to the teeth when the active layer becomes hydratedaids in the gentle abrasive cleaning effect of stains from the teeth as mild abrasive action from the gums pressing the active layer against the teeth as the strip is worn. For example, dental or pharmaceutical grades of titanium dioxide, talc, zinc oxide etc. and preferably surface treated titanium dioxide such as MPY-18S, available from Tayca Corp., Okayama Japan may be used alone or in combination at levels (by weight) of up to 10%, i.e. 1-10%, most preferably about 5%.

Magnesium Hydroxide or Sodium Hydroxide (USP or Food Grade) can be used to adjust the pH of the active layer.

The best mode for carrying out the invention is detailed in the following example:

| Active Layer Formulation | Parts |
|---|---|
| Deionized or Distilled Water | 11.2 |
| Add the following to the water phase with moderate mixing | |
| Magnesium Sulfate | 4 |
| Sodium Acid Pyrophosphate | 4 |
| Heat to 125 degrees F. | |
| Mix smooth | |
| Turn off heat | |
| Add Glycerin | 7.5 |
| Premix Glycosperse Q-20 | 1 |
| & Propylene Glycol | 12 |
| Add to master liquid and | |
| Mix smooth | |
| Add Dextrin D-400 | 26 |
| Mix smooth | |
| Add 35% Hydrogen Peroxide | 10 |
| Mix smooth | |
| Add Dextrin D-400 | 25 |
| Mix smooth | |
| Add 35% Hydrogen Peroxide | 10 |
| Mix smooth | |
| Add Mint Scent | 0.3 |

Properties

Theoretical peroxide content is 7%

Active Hydrogen peroxide level was determined by peroxide indicator paper to be nominally 6% with approximately 1% lost through bleaching.

Solids of the formulation are 67.5% less water, peroxide and propylene glycol.

pH of the formulation above is 3.7 Adjust pH with magnesium hydroxide USP (or equivalent) (8 wt % solution) to bring the pH to a level of 5-6. 0.8% magnesium hydroxide addition raised the pH to 4.2. 0.95% magnesium hydroxide raised the pH to 5.1. 1.1% magnesium hydroxide raised the pH to 6.1.

Viscosity 7,000 cps-12,000 cps

Thereof.

Active peroxide whitening agent concentration is adjusted by varying the amount of hydrogen peroxide solution added.

In a preferred embodiment, before the addition of the peroxide, the temperature of the coating formulation is raised to 165° F. and held for minutes to eradicate any bacteria, fungi, mold or mixtures thereof. The heated whitening composition is then cooled to below 90° F. before proceeding with the peroxide addition.

The solution above is coated onto corona treated 2 mil white low density polyethylene barrier support film at a deposition of 55 grams/1000 sq. in dry (approximately 3 mils of active layer) for an overall strip thickness of 5 mils using conventional film coating equipment using a film that is about 40 cm wide. The barrier support with the active layer is laminated to a 3 mil clear polyester silicone (food or pharmaceutical grade) release coated carrier and is subsequently cut to size. The size is not critical and may be from about 1.0 to 3.0 cm by about 3 to 6 cm. Other sizes may also be used especially if the whitening strips are to be used for veterinary purposes. Flexural stiffness (Gurley stiffness) measurements of the barrier support layer with the active layer removed from the carrier are nominally 6.5 grams/centimeter as measured on a Handle-O-Meter, available from Thwing-Albert Instrument Co.

Determining the % volatiles of the hybrid strip.

1—Determine the total weight of the strip including the barrier support layer and active layer with the carrier layer removed. This value is identified as A 2—Dry the strip in an oven at 170° F. for 1 hour to make it bone dry 3—Remove the strip from the oven and quickly weigh again to determine the bone dry weight. This value is identified as B 4—Wash off the active layer with water and a towel and then dry.

5—Weight the barrier support film. This value is identified as C

The % total volatiles is A-B/A-C

Determining % Peroxide volatiles of the hybrid strip

1—Determine the weight of a strip comprising the barrier support and active layer removed from the carrier. This value is identified as D.

2—Wash off the active layer from the barrier support into 25 grams of water in a beaker taking care to remove all the active layer into the water.

3—Dry the barrier support with the active layer removed and determine the weight. This value is identified as E.

4—To determine the weight of active layer removed from the strip now in the 25 grams of water, calculate F as D minus E. F=(D−E)

5—Using a peroxide test paper strip called Merckoquant® available from EMD Chemicals Inc., Gibbstown N.J., perform the following procedure:

The peroxide test strip contains at one end, two reaction zones as square indicator patches. One is used as a the peroxide color indicator to compare against the concentration versus color standards in the range of 0-1000 ppm on the container the strips are supplied in. The second indicator is used to determine if the concentration of the measurement solution exceeds the maximum test range of the strip. This indicator must not turn color.

Immerse both reaction zones into the measurement solution for 1 second. Allow excess solution to run off via the long edge of the test strip on an absorbent material. Wait 30 seconds and then compare with the color concentration scale and read the resultant value G in ppm.

To determine the actual percent of Hydrogen Peroxide present in the active layer called X that was diluted in 25 grams of water, the following formula is used:

$$X = (25\ G + GF)/F\ 10{,}000)$$

Where X=% actual peroxide in the active layer
F=weight of active layer removed
25=dilution water
G=ppm from test strip indicator scale
All percents are by weight.

We claim:

1. A dental whitening strip which comprises a three layer laminated structure where a first layer is a barrier support comprising a polyolefin polymer film in contact with a second and middle layer which is a whitening composition which adheres to said barrier support said whitening composition comprising a dried layer that is formed from a whitening composition comprising: (a) dextrin; (b) a peroxide; (c) a non-toxic water soluble inorganic salt; (d) a pharmaceutically acceptable hydroxy compound which is a plasticizer and (e) an amount of water to enable the whitening composition to be adhered to a third layer which is a carrier layer said whitening composition being dried so that it does not flow, does not wet objects and has retained volatiles between 7 and 17% as determined by drying in an oven at 170° F. for 1 hour wherein the whitening composition comprises from 1 to 20 wt % of the total weight of the whitening strip not including the carrier layer.

2. A dental whitening strip as defined in claim 1 where the peroxide is an inorganic peroxide.

3. A dental whitening strip as defined in claim 2 wherein said peroxide is selected from the group consisting of hydrogen peroxide, carbamide peroxide, calcium peroxide, sodium percarbonate, sodium perborate and tetrasodium pyrophosphate peroxidate.

4. A dental whitening strip as defined in claim 1 wherein the pharmaceutically acceptable hydroxy compound which is a plasticizer is selected from the group consisting of glycerin, propylene glycol, polyethylene glycol, polyethylene oxide; sorbitol; carbopol; polaxamer; povidone, polyvinyl alcohol and mixtures of any combination thereof.

5. A dental whitening strip as defined in claim 1 wherein the whitening composition includes an inorganic fluoride in a non-toxic amount which will reduce the incidence of dental decay when applied to the teeth.

6. A dental whitening strip as defined in claim 1 wherein the barrier support is an extruded polymer film.

7. A dental whitening strip as defined in claim 6 wherein the barrier film comprises a polyethylene film.

8. A dental whitening strip as defined in claim 1 wherein said whitening strip is sized to fit within the oral cavity of an end user.

9. A whitening composition for a dental strip which comprises a composition consisting of: (a) dextrin; (b) a peroxide; (c) a non-toxic water soluble inorganic salt; (c) a acceptable hydroxy compound which is a plasticizer; and (d) water, said whitening composition being dried so that it does not flow, does not wet objects and has retained volatiles between 7 and 17% as determined by drying in an oven at 170° F. for 1 hour.

10. A dental whitening composition as defined in claim 9 where the peroxide is an inorganic peroxide.

11. A dental whitening composition as defined in claim 9 wherein said peroxide is selected from the group consisting of hydrogen peroxide, carbamide peroxide, calcium peroxide, sodium percarbonate, sodium perborate, and tetrasodium pyrophosphate peroxidate.

12. A dental whitening composition as defined in claim 9 wherein the pharmaceutically acceptable hydroxy compound which is a plasticizer is selected from the group consisting of glycerin, propylene glycol, polyethylene glycol, polyethylene oxide, sorbitol; carbopol; polaxamer; povidone, polyvinyl alcohol and mixtures of any combination thereof.

13. A dental whitening composition as defined in claim 9 which includes an inorganic fluoride in a non-toxic amount which will reduce the incidence of dental decay when applied to the teeth.

14. A dental whitening composition as defined in claim 9 wherein the whitening composition comprises: (a) from 10-75 wt % dextrin; (b) from 2-20 wt % of a peroxide; (c) from 2-20 wt % of a' non-toxic water soluble inorganic salt; (c) from 1-10 wt % of a hydroxy compound which is a plasticizer; and (d) water balance to 100 wt %.

15. A dental whitening composition as defined in claim 14 which comprises: (a) from 20-65 wt % dextrin; (b) from 2-20 wt % of hydrogen peroxide; (c) from 2-20 wt % of a non-toxic water soluble inorganic salt selected from magnesium sulfate, sodium acid pyrophosphate and mixtures thereof; (c) from 1-10 wt % of glycerin, propylene glycol or a mixture thereof; and (d) water balance to make 100 wt %.

16. A dental whitening composition as defined in claim 14 which includes from 1-10 wt % of an abrasive filler which aids in polishing the teeth.

17. A dental whitening strip which consists of a three layer laminated structure where a first layer is a barrier support which consists of polyethylene, said barrier support being in contact with a second layer consisting of a whitening composition, said whitening composition comprising a dried layer that is formed from a whitening composition, said dried layer being a layer that does not flow, does not wet objects and has retained volatiles between 7 and 17% as determined by drying in an oven at 170° F. for 1 hour and is formed by coating and drying on said barrier layer, wherein said whitening composition comprising: (a) dextrin; (b) a peroxide; (c) a non-toxic water soluble inorganic salt; d) a pharmaceutically acceptable hydroxy compound which is a plasticizer and (e) an amount of water to enable the whitening composition to be adhered to a third layer consisting of a carrier layer consisting of a film made of a material selected from the group consisting of polypropylene, polyethylene, polyester, polyvinyl chloride, polytetrafluoroethylene and copolymers or blends thereof wherein the whitening composition comprises from 1 to 20 wt % of the total weight of the whitening strip not including the carrier.

* * * * *